(12) United States Patent
Shimotsu

(10) Patent No.: US 8,343,044 B2
(45) Date of Patent: Jan. 1, 2013

(54) LIGHT GUIDE FOR ENDOSCOPES

(75) Inventor: Shinichi Shimotsu, Kanagawa-ken (JP)

(73) Assignee: Fujifilm Corporation (JP)

( * ) Notice: Subject to any disclaimer, the term of this patent is extended or adjusted under 35 U.S.C. 154(b) by 788 days.

(21) Appl. No.: 12/482,840

(22) Filed: Jun. 11, 2009

(65) Prior Publication Data

US 2009/0312609 A1   Dec. 17, 2009

(30) Foreign Application Priority Data

Jun. 12, 2008   (JP) .................................. 2008-153718

(51) Int. Cl.
*A61B 1/07* (2006.01)
*G02B 6/04* (2006.01)

(52) U.S. Cl. ............ 600/182; 362/574; 385/43; 385/115
(58) Field of Classification Search .................. 600/182; 362/572–574; 385/43, 76, 115, 116
See application file for complete search history.

(56) References Cited

U.S. PATENT DOCUMENTS

| | | | | |
|---|---|---|---|---|
| 3,779,628 A | * | 12/1973 | Kapron et al. .................... 385/43 |
| 3,874,783 A | * | 4/1975 | Cole ............................. 385/115 |
| 4,272,156 A | * | 6/1981 | Ishibashi et al. ............... 385/117 |
| 4,615,333 A | * | 10/1986 | Taguchi ........................ 600/171 |
| 4,815,816 A | * | 3/1989 | Schneider ..................... 385/116 |
| 4,867,136 A | | 9/1989 | Suzuki et al. |
| 4,870,950 A | | 10/1989 | Kanbara et al. |
| 4,953,937 A | * | 9/1990 | Kikuchi et al. ................. 385/33 |
| 5,239,026 A | * | 8/1993 | Babirad et al. ................. 526/245 |
| 5,371,826 A | * | 12/1994 | Friedman ....................... 385/115 |
| 5,373,571 A | * | 12/1994 | Reid et al. ...................... 385/31 |
| 5,438,873 A | * | 8/1995 | Wlodarczyk et al. ............ 73/705 |
| 5,513,291 A | * | 4/1996 | Buchin et al. .................... 385/93 |
| 5,800,343 A | * | 9/1998 | Takeuchi et al. ............... 600/132 |
| 5,919,130 A | * | 7/1999 | Monroe et al. ................. 600/200 |
| 5,953,477 A | * | 9/1999 | Wach et al. .................... 385/115 |

(Continued)

FOREIGN PATENT DOCUMENTS

JP       S61-85805 U       6/1986

(Continued)

OTHER PUBLICATIONS

Japanese Office Action "First Notification of Grounds for Rejection" dated Jul. 31, 2012; Japanese Application No. 2008-153718; with partial English translation.

*Primary Examiner* — John P Leubecker
(74) *Attorney, Agent, or Firm* — Studebaker & Brackett PC; Donald R. Studebaker

(57) ABSTRACT

A light guide for endoscopes is constituted by a plurality of multimode optical fibers, of which at least a portion is bundled. The light guide propagates illuminating light beam that enters from a first end facet thereof to a second end facet thereof, to emit the illuminating light beam onto a portion to be observed. The light guide includes: a light input portion formed by the bundled plurality of multimode optical fibers; and a light output portion formed by the bundled plurality of multimode optical fibers. At least one of the light input portion and the light output portion is shaped in a tapered shape, while the number of multimode optical fibers at the light input portion and the light output portion are the same as that at other portions of the light guide.

17 Claims, 6 Drawing Sheets

U.S. PATENT DOCUMENTS

| | | | |
|---|---|---|---|
| 6,208,788 B1* | 3/2001 | Nosov | 385/121 |
| 6,434,302 B1* | 8/2002 | Fidric et al. | 385/43 |
| 6,438,302 B1 | 8/2002 | Utsui et al. | |
| 6,478,732 B2* | 11/2002 | Adachi | 600/178 |
| 6,628,876 B1* | 9/2003 | Shmulovich | 385/129 |
| 7,006,220 B2* | 2/2006 | Bambot et al. | 356/338 |
| 7,731,710 B2* | 6/2010 | Smith | 606/16 |
| 7,957,432 B2* | 6/2011 | Seo et al. | 372/6 |
| 2001/0031115 A1* | 10/2001 | Chen et al. | 385/54 |
| 2002/0007111 A1* | 1/2002 | Deckert et al. | 600/177 |
| 2003/0021124 A1* | 1/2003 | Elbrecht et al. | 362/572 |
| 2003/0163030 A1* | 8/2003 | Arriaga | 600/182 |
| 2006/0250814 A1* | 11/2006 | Tabor | 362/551 |
| 2006/0257083 A1* | 11/2006 | Rasmussen | 385/115 |
| 2007/0237453 A1* | 10/2007 | Nielsen et al. | 385/28 |
| 2008/0037933 A1* | 2/2008 | Furman et al. | 385/31 |

FOREIGN PATENT DOCUMENTS

| | | |
|---|---|---|
| JP | S63-265215 A | 11/1988 |
| JP | 6-296584 A | 10/1994 |
| JP | H10-239029 A | 9/1998 |
| JP | 2001-8892 A | 1/2001 |
| JP | 2002-289016 A | 10/2002 |

* cited by examiner

PRIOR ART

INPUT RANGE OF LIGHT FROM FOCUSING OPTICAL SYSTEM

INPUT RANGE OF LIGHT FROM FOCUSING OPTICAL SYSTEM

LIGHT GUIDE FOR ENDOSCOPES

BACKGROUND OF THE INVENTION

1. Field of the Invention

The present invention is related to a light guide for endoscopes, that is, a light guide that propagates light therethrough such that portions which are observed with an endoscope are illuminated.

2. Description of the Related Art

Conventionally, endoscopes are in wide use to observe and perform surgical procedures on portions within body cavities of humans. Flexible light guides for illuminating the observed portions of subjects are employed in these endoscopes. Note that in cases that surgical procedures are performed on portions, observation thereof is necessary. Therefore, portions on which surgical procedures are performed will also be referred to as "observed portions" in the present specification.

At least a portion of this type of light guide is generally constituted by a plurality of thin multi mode optical fibers which are bundled, to impart flexibility thereto. Japanese Unexamined Patent Publication No. 6 (1994)-296584 discloses an example of a light guide for endoscopes configured in this manner. This light guide for endoscopes receives illuminating light beam, by the illuminating light beam being emitted from an illuminating light source, focused, then irradiated on a first end facet of the light guide. The illuminating light beam propagates through the light guide and is emitted from a second end facet to illuminate an observed portion.

Administering glass forming at the light input portions and the light output portions of conventional light guides for endoscopes such that they are maximally densely filled, that is, the spaces among the optical fibers at these portions are minimal, is being considered. Glass forming is a technique in which external pressure is applied to a plurality of bundled multi mode optical fibers while heating them at temperatures less than or equal to a glass softening temperature so as to densely assemble the optical fibers.

FIG. 10 is a sectional diagram that illustrates a maximally densely filled structure formed in the manner described above. FIG. 11 is a diagram that illustrates an example of a light guide 5 for endoscopes that employs the maximally densely filled structure. In FIG. 10 and FIG. 11, reference numeral 11 denotes a plurality of multi mode optical fibers, and reference number 12 denotes a filling adhesive for fixing the multimode optical fibers 11 in a bundled state such that the maximally densely filled structures can function as connector portions. Reference numeral 3 of FIG. 11 denotes a reinforcing structure for reinforcing the portion onto which glass forming has been administered. The reinforcing structure 3 is provided, because the multi mode optical fibers 11 become frangible by applying heat and pressure as described above. Reference numeral 6 of FIG. 11 denotes an illuminating light source for emitting an illuminating light beam 7, reference numeral 8 denotes a focusing optical system for focusing the illuminating light beam 7 and causing it to enter the plurality of multimode optical fibers 11 from a side towards first facets (light input facets) thereof, and reference numeral 9 denotes an optical element which is provided in close contact with the second facets (light output facets) of the multi mode optical fibers 11.

There is a problem that first facets that function as light input portions and second facets that function as light output portions of conventional light guides for endoscopes, which are constituted by bundling a plurality of thin optical fibers together, are easily damaged.

In addition, it is desirable for the light output portions of light guides for endoscopes to have greater numerical apertures, such that illuminating light beams can be emitted with a wide angle of spread to illuminate greater areas of observed portions. Meanwhile, it is also desirable for the light input facets of the light guides to have greater numerical apertures, such that the light receiving angle thereof (corresponding to the angle of spread at the light output facet) becomes great to increase the utilization efficiency of the illuminating light beams. There is still room for improvement in conventional light guides for endoscopes in the point of increasing the numerical apertures of the light input portions and the light output portions.

SUMMARY OF THE INVENTION

The present invention has been developed in view of the foregoing circumstances. It is an object of the present invention to provide a light guide for endoscopes having a light input portion and a light output portion formed by bundling a plurality of optical fibers, which are not prone to damage and which have greater numerical apertures.

A light guide for endoscopes of the present invention is a light guide constituted by a plurality of multimode optical fibers, of which at least a portion is bundled, for propagating an illuminating light beam that enters from a first end facet thereof to a second end facet thereof, to emit the illuminating light beam onto a portion to be observed. The light guide comprises: a light input portion (a portion toward the interior of the light guide from the first end facet, which functions as a light input surface) formed by the bundled plurality of multimode optical fibers; and a light output portion (a portion toward the interior of the light guide from the second end facet, which functions as a light output surface) formed by the bundled plurality of multimode optical fibers. At least one of the light input portion and the light output portion is shaped in a tapered shape, while the number of multimode optical fibers at the light input portion and the light output portion are the same as that at other portions of the light guide.

Note that it is desirable for the tapering rate of the light input portion to be less than 36%. Note that here, the tapering rate is defined as (a diameter which has been decreased by tapering)/(a diameter prior to tapering).

It is particularly desirable for the light guide for endoscopes of the present invention to further comprise: a concave transparent member, which is provided in close contact with the second end facet.

In multi mode fibers, there is a relationship that the product of the beam diameter (core diameter) of an input or output light beam and the angle of beam spread $\theta$ is maintained. Note that the numerical apertures of optical fibers are defined as $NA = \sin \theta$. In the light guide for endoscopes of the present invention, at least one of the light input portion and the light output portion, which are constituted by a plurality of bundled multi mode optical fibers, is of a tapered shape, while having the same number of optical fibers as at other portions of the light guide. Therefore, the core diameter at the light input portion and/or the light output portion is smaller than that of the other portions.

Based on the aforementioned relationship, the angle of beam spread $\theta$ at the light input portion and/or the light output portion will become greater, that is, the numerical aperture will become greater. Therefore, the illuminating light beam will enter the light input portion with greater light utilization efficiency, and wider areas of observed portions can be illuminated at the light output portion. FIG. 12A and FIG. 12B are diagrams for facilitating understanding of this phenomenon. In FIG. 12A and FIG. 12B, reference numeral 11 denotes a multi mode optical fiber, reference numeral 11a denotes the core of the multi mode optical fiber 11. FIG. 12A illustrates a case in which no taper is provided, and FIG. 12B illustrates a case in which the multi mode optical fiber 11 is tapered. Here, a case is illustrated in which there is only one optical fiber. However, the principle applies in cases that a plurality of optical fibers are bundled.

In addition, by forming the light input portion and/or the light output portion into tapered shapes, these portions become resistant to damage. This point will be described in detail below. FIG. 13 is a diagram that schematically illustrates the cross section of an end portion of a conventional light guide for endoscopes that functions as a light input portion or a light output portion. As illustrated in FIG. 13, a plurality of multi mode optical fibers 11 are bundled and fixed by a filling adhesive 12 at the end portion. The end portion is housed within a cylindrical connector housing, for example. According to research by the present inventor, it was found that it is difficult to arrange the plurality of multi mode optical fibers 11 into a maximally densely filled structure. That is, as illustrated in FIG. 13, it was unavoidable for the filling adhesive 12 to be present within the spaces among the multi mode optical fibers 11. For this reason, when the properties of the filling adhesive 12 deteriorate over time, the entirety of the end portion of the light guide becomes prone to damage.

In contrast, at least one end portion of the light guide for endoscopes of the present invention, that is, the light input portion and/or the light output portion, is tapered, while having the same number of optical fibers as the other portions thereof. Therefore, the cross section of the end portion of the light guide for endoscopes of the present invention becomes that illustrated in FIG. 2. In this case, the plurality of multi mode optical fibers 11 become a maximally densely filled structure or approaches a maximally densely filled structure, and the filling adhesive 12 is not present among the optical fibers, or only a small amount of the filling adhesive 12 is present among the optical fibers. Therefore, the end portion of the light guide, that is, the light input portion and/or the light output portion, becoming prone to damage due to deterioration of the filling adhesive 12 can be prevented.

Note that in the conventional light guide 5 for endoscopes illustrated in FIG. 10 and FIG. 11 as well, the plurality of multi mode optical fibers 11 become a maximally densely filled structure. Therefore, it may be said that the problem of decrease in structural strength due to deterioration of the filling adhesive 12 may not occur in the conventional light guide 5 for endoscopes. However, the reinforcing structure 3 is provided to compensate for the decrease in structural strength due to glass forming. Therefore, the light guide for endoscopes becomes difficult to bend at this portion. Specifically, there are cases in which an unbendable portion of the light guide will become as long as 10 cm or greater due to the presence of the reinforcing structure 3. In these cases, there is a possibility that the observation performance may decrease in particularly small endoscopes to be inserted into body cavities.

In contrast, the light guide for endoscopes of the present invention does not require glass forming, and therefore, the aforementioned reinforcing structure is not necessary. Accordingly, the problem of decreased observation performance due to a long unbendable portion being present can be avoided.

In the light guide for endoscopes of the present invention, the tapering rate of the light input portion may be less than 36%. In this case, the loss caused due to the tapered shape can be suppressed to a degree that does not cause any practical problems. A detailed explanation of the reasons why loss can be suppressed will be given in the description of the embodiments of the present invention.

The light guide for endoscopes of the present invention may further comprise a concave transparent member, which is provided in close contact with the second end facet that functions as a light output surface of the illuminating light beam. In this case, the illuminating light beam which is output from the second end facet is diffused by the effect of the concave shape of the transparent member. Accordingly, an advantageous effect that the illuminated range can become even wider is obtained.

BEST MODE FOR CARRYING OUT THE INVENTION

Hereinafter, embodiments of the present invention will be described in detail with reference to the attached drawings.

Figure 1:
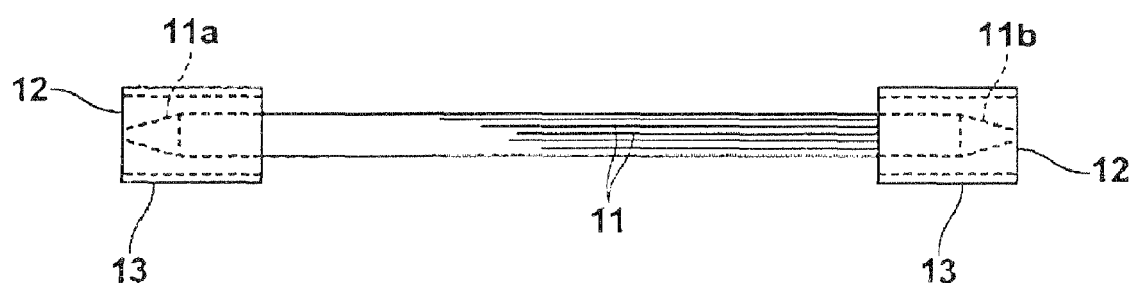
FIG. 1 is a side view that illustrates a light guide for endoscopes according to a first embodiment of the present invention.

FIG. 1 is a side view that illustrates a light guide 10 for endoscopes according to a first embodiment of the present invention. The light guide 10 for endoscopes is constituted by a plurality of bundled multi mode optical fibers 11 across its entire length. A first end portion 11a (toward the left in FIG. 1) and a second end portion 11b (toward the right in FIG. 1) of the bundled multi mode optical fibers 11 are housed in cylindrical connector housings 13, and fixed therein by a filling adhesive 12.

The first end portion 11a and the second end portion 11b are both of tapered shapes. The first end portion 11a functions as a light input portion, the facet of which an illuminating light beam enters through. The second end portion 11b functions as a light output portion, the facet of which the illuminating light beam is output through. Note that the number of optical fibers 11 at the tapered first end portion 11*a* and the tapered second end portion 11*b* is the same as at the other portions of the light guide 10.

Figure 11:
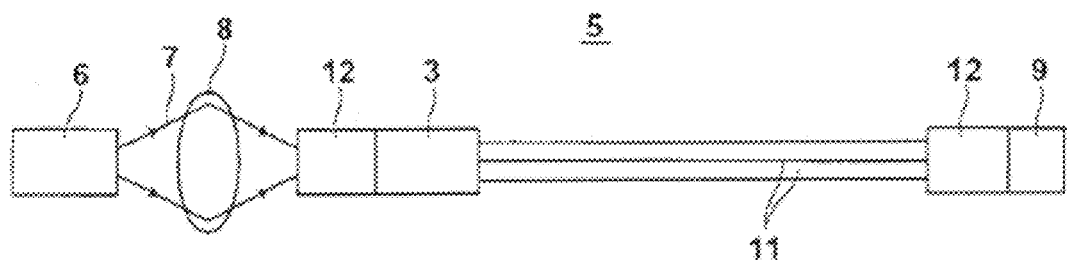
FIG. 11 is a side view that illustrates an example of a conventional light guide for endoscopes.
Figure 12A:
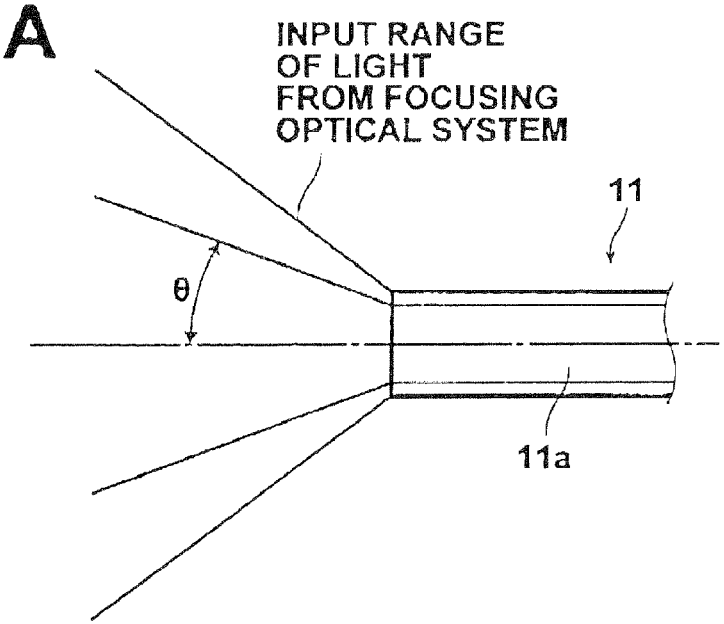
FIG. 12A and FIG. 12B are diagrams for explaining the advantageous effects of the present invention.
Figure 12B:
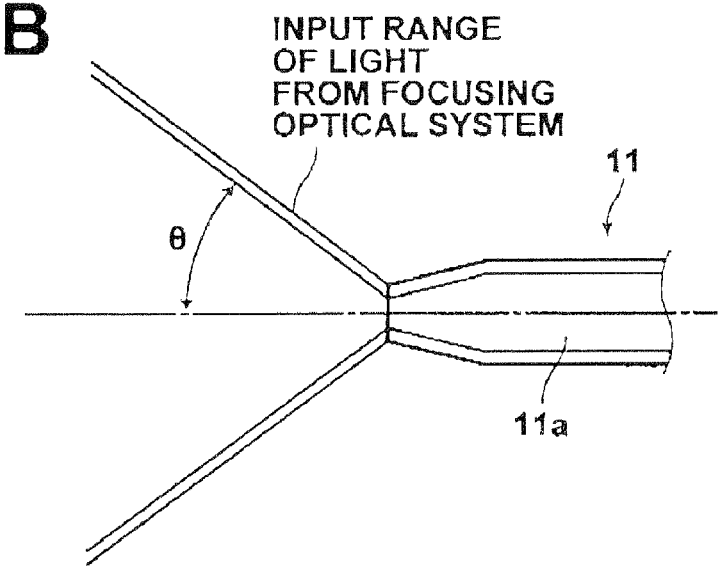
Figure 13:
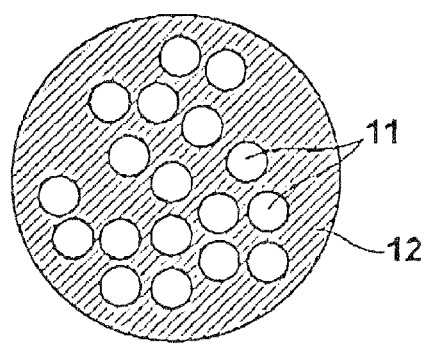
FIG. 13 is a diagram that schematically illustrates the cross section of a portion of a conventional light guide for endoscopes.

The light guide 10 for endoscopes having the construction as described above is utilized in the same manner as the light guide for endoscopes illustrated in FIG. 11. That is, the illuminating light beam is focused, then irradiated on the facet of the first end portion 11*a*. The illuminating light beam propagates through the light guide 10 and is emitted from the facet of the second end portion 11*b*, to illuminate an observed portion within a body cavity of a human subject.

Figure 3A:
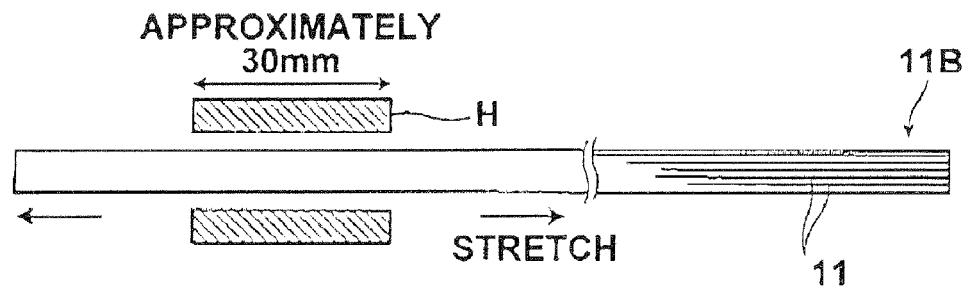
FIGS. 3A, 3B, 3C, 3D, and 3E are diagrams for explaining a method for producing the light guide for endoscopes of FIG. 1.
Figure 3B:
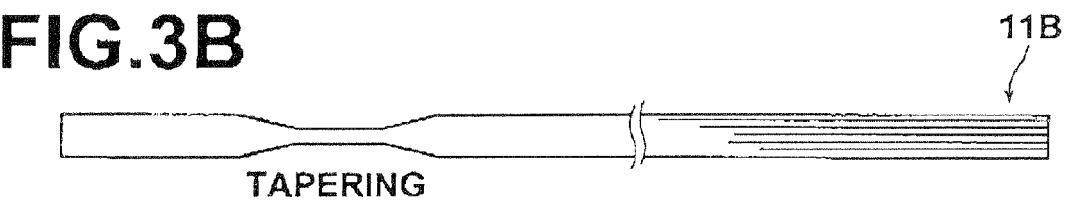
Figure 3C:
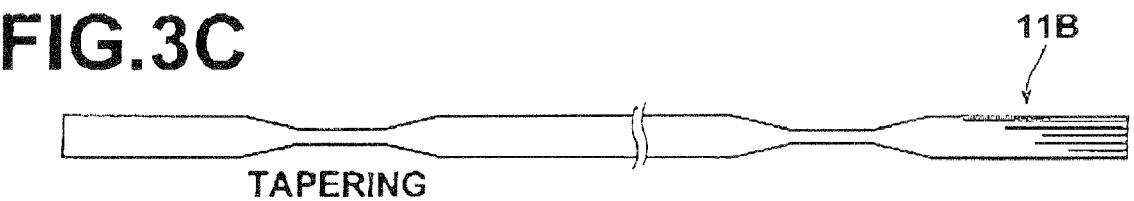
Figure 3D:
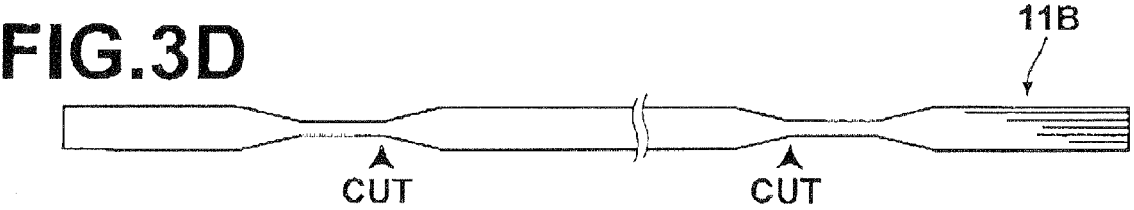
Figure 3E:
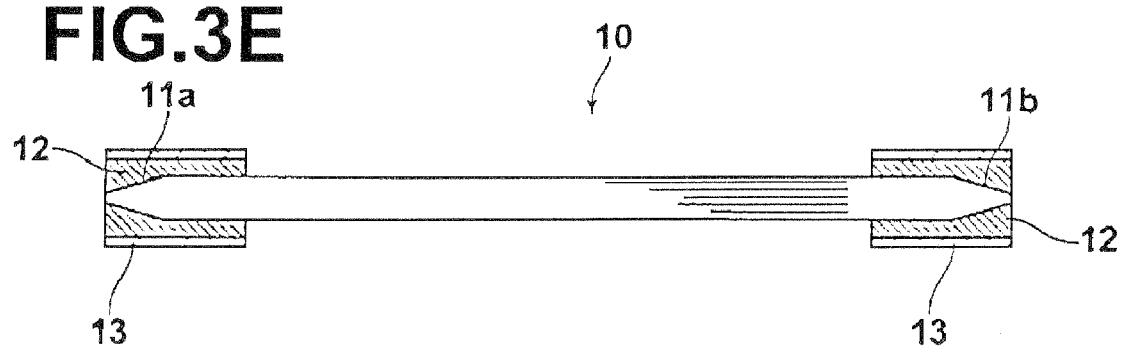

Next, a method for producing the light guide 10 for endoscopes having the above construction will be described with reference to FIGS. 3A, 3B, 3C, 3D, and 3E. First, a bundle 11B, which is an assembly of a plurality of thin diameter multi mode optical fibers 11, is prepared. A portion thereof is heated to 500° C. or greater, for example, by a heater H having a heating length of approximately 30 mm, and the heated portion is stretched and elongated (FIG. 3A). Thereby, the heated and stretched portion of the bundle 11B becomes tapered (FIG. 3B). Next, another portion of the bundle 11B is processed in the same manner as above, and the other portion becomes tapered as well (FIG. 3C). Next, the bundle 11B is cut at the two tapered portions (FIG. 3D). Thereafter, the tapered first end portion 11*a* and the tapered second end portion 11*b* are housed within the connector housings 13. The gap between the first end portion 11*a* and the connector housing 13 as well as the gap between the second end portion 11*b* and the connector housing 13 are filled with the heat curing filling adhesive 12 and fixed therein. Finally, the facets of the end portions 11*a* and 11*b* are optically polished, and the light guide 10 for endoscopes is completed (FIG. 3E).

Note multi mode optical fibers that have outer diameters of 80 μm or less including the cladding portions thereof, and core diameters of 60 μm to 70 μm, for example, may be employed favorably as the multi mode optical fibers 11. The lengths of the tapered portions at the first end portion 11*a* and the second end portion 11*b* are approximately 15 mm, which is a length which is capable of being housed within common connector housings.

In the light guide 10 for endoscopes according to the first embodiment, the first end portion 11*a* and the second end portion 11*b* are of tapered shapes. Therefore, the cross section of the end portions becomes that illustrated in FIG. 2. In this case, the plurality of multi mode optical fibers 11 become a maximally densely filled structure or approaches a maximally densely filled structure, and the filling adhesive 12 is not present among the optical fibers, or only a small amount of the filling adhesive 12 is present among the optical fibers. Therefore, the first end portion 11*a* and the second end portion 11*b* becoming prone to damage due to deterioration of the filling adhesive 12 can be positively prevented.

In addition, the reinforcing structure 3 illustrated in FIG. 11 is not necessary in the light guide 10 for endoscopes. Therefore, no portions which are unbendable due to the presence of the reinforcing structure are generated, and favorable observation performance can be secured.

Note that in the first embodiment described above, both the first end portion 11*a* and the second end portion 11*b* of the light guide 10 for endoscopes are tapered in shape. However, even in the case that only one of the end portions is tapered in shape, the aforementioned advantageous effects can be obtained at the tapered end portion.

In light guides for endoscopes, of which a portion is not constituted by a plurality of bundled multi mode optical fibers, in the case that at least one of a first end portion and a second end portion thereof is formed by bundling a plurality of multi mode optical fibers, the tapered shape may be applied to the end portions. Thereby, the advantageous effects described above can be obtained.

Further, only the tapered first end portion and/or the tapered second end portion may be produced, and a first end portion and/or a second end portion of an existing light guide for endoscopes may be replaced with the tapered end portions. Thereby, the existing light guide for endoscopes may be improved to exhibit the advantageous effects described above.

Figure 4:
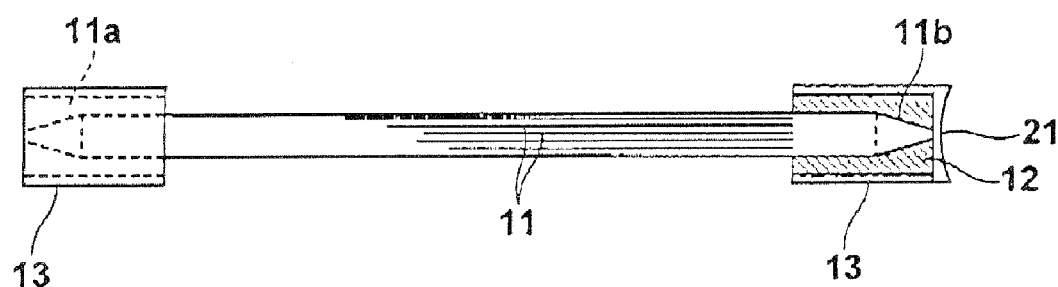
FIG. 4 is a partially sectional side view of a light guide for endoscopes according to the second embodiment of the present invention.

Next, a second embodiment of the present invention will be described with reference to FIG. 4. FIG. 4 is a partially sectional side view of a light guide 20 for endoscopes according to the second embodiment of the present invention. Note that in FIG. 4, elements which are the same as those illustrated in FIG. 1 and FIG. 2 are denoted with the same reference numerals, and detailed descriptions thereof will be omitted insofar as they are not particularly necessary (the same will apply to all subsequent embodiments).

Figure 2:
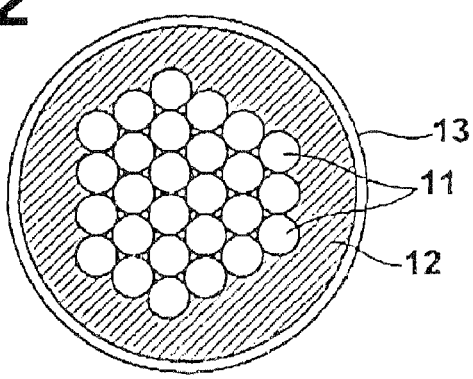
FIG. 2 is a sectional diagram that illustrates a portion of the light guide for endoscopes of FIG. 1.

The light guide 20 for endoscopes of the second embodiment differ from the light guide 10 for endoscopes illustrated in FIG. 1 and FIG. 2 in that a concave transparent member 21 is provided in close contact with the end facet of the second end portion 11*b*. By the transparent member 21 being provided, the illuminating light beam which is output from the end facet of the second end portion 11*b* is diffused by the effect of the concave shape of the transparent member 21. Accordingly, an advantageous effect that the illuminated range can become even wider is obtained.

Figure 5:
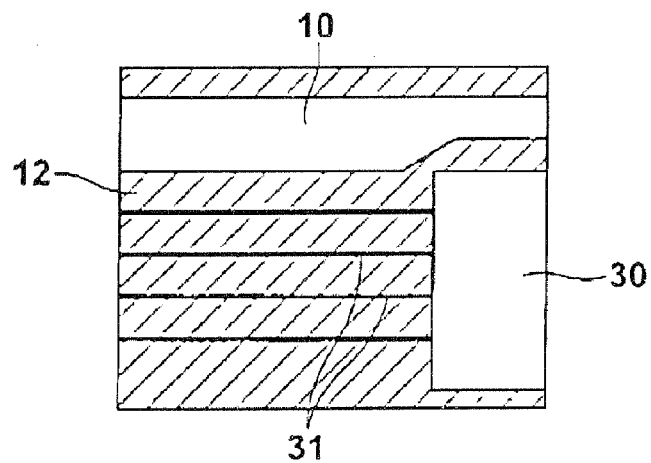
FIG. 5 is a sectional side view of the front end portion of an endoscope, equipped with the light guide of the present invention.
Figure 6:
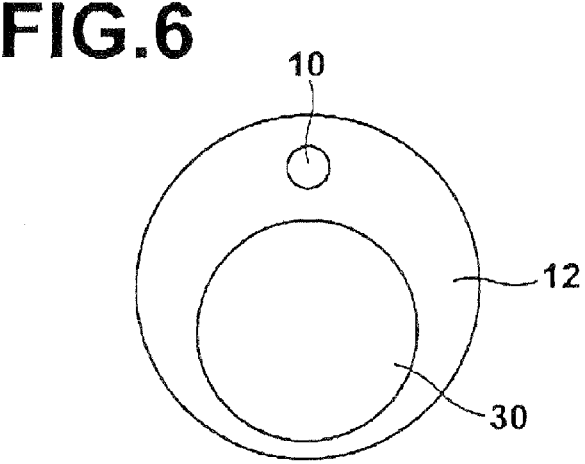
FIG. 6 is a front view of the front end portion of the endoscope of FIG. 5.
Figure 7:
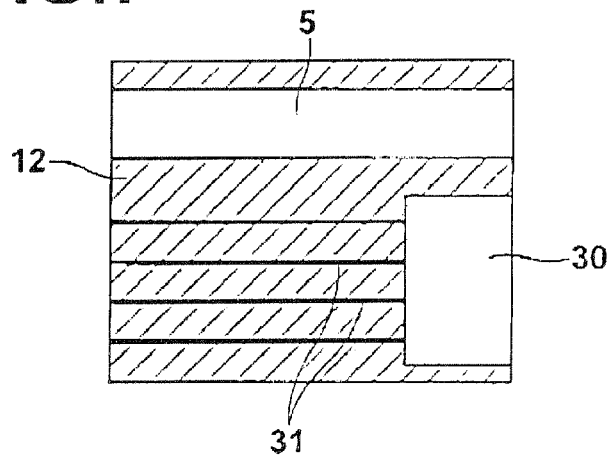
FIG. 7 is a sectional side view of the front end portion of an endoscope, equipped with a conventional light guide of the present invention.
Figure 8:
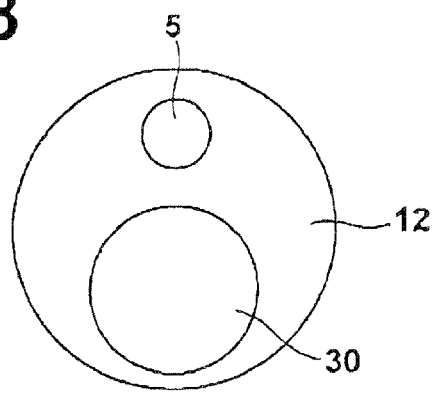
FIG. 8 is a front view of the front end portion of the endoscope of FIG. 7.

Next, another advantageous effect which is obtained by the present invention will be described. FIG. 5 is a sectional side view of the front end portion of an endoscope, equipped with the light guide 10 of the present invention and an imaging element 30 such as a CCD for obtaining images of illuminated observed portions. FIG. 6 is a front view of the front end portion of the endoscope of FIG. 5. Note that reference numeral 31 of FIG. 5 denotes wires for connecting the imaging element 30 with circuitry (not shown). FIG. 7 is a sectional side view of the front end portion of an endoscope, equipped with a conventional light guide 5, of which the end portion is not tapered, and an imaging element 30 such as a CCD for obtaining images of illuminated observed portions. FIG. 8 is a front view of the front end portion of the endoscope of FIG. 7.

As is clear when comparing FIGS. 5 and 6 against FIGS. 7 and 8, if the front end portion of the light guide 10, which is constituted by a plurality of multi mode fibers, is tapered, a larger imaging element 30 may be employed to the extent that the imaging element 30 does not interfere with the front end portion of the light guide 10. Further, there is a greater degree of freedom for the layout of the imaging element 30.

In the case that other components other than the imaging element 30 are provided at the front end portion of an endoscope, if the front end portion of the light guide is tapered, a greater amount of space can be secured to provide the other components in. Therefore, the advantageous effects that larger components may be employed, and that greater degrees of freedom for the layout thereof are possible, are obtained.

Figure 9:
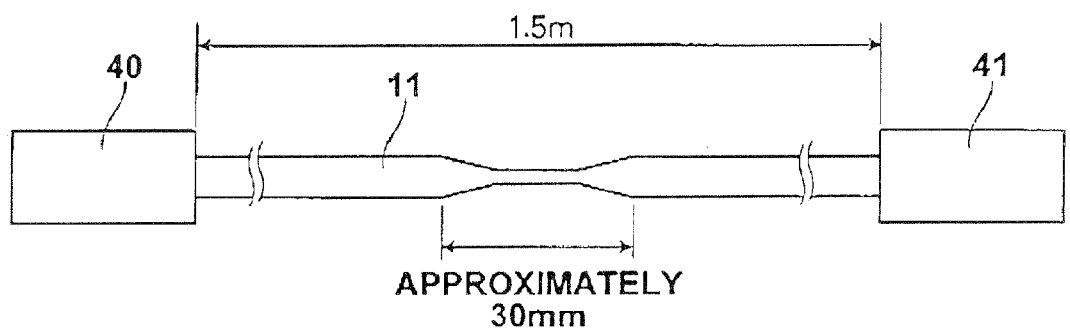
FIG. 9 is a schematic side view that illustrates a system for evaluating the light guide for endoscopes of the present invention.
Figure 10:
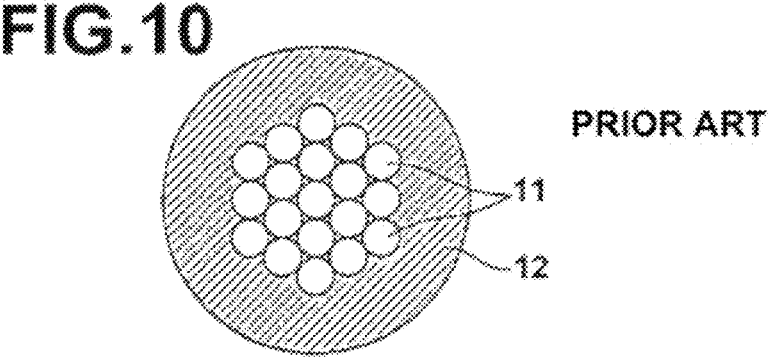
FIG. 10 is a sectional diagram that illustrates a portion of a conventional light guide for endoscopes.

Next, favorable taper shapes for the light input portion and the light output portion of the light guide for endoscopes of the present invention will be described. As illustrated in FIG. 9, a first end portion of a multi mode optical fiber 11 having an outer diameter of 125 μm and a length of 1.5 m was connected to a laser light emitting system 40, and a second end portion thereof was connected to a photodetector 4, to produce an evaluating system. The central portion of the multi mode optical fiber 11 was heated across a range of 30 mm and stretched, to form a tapered portion. Five evaluating systems were produced, with stretched lengths of 0 mm (zero, no extension), 1 mm, 3 mm, 6 mm, and 8 mm.

Evaluations were performed as follows. Laser beams having a wavelength of 633 nm were emitted from the laser light emitting system 40 of each evaluating system, and caused to enter the multi mode optical fibers 11 to propagate therethrough. The intensities of the laser beams which were output from each of the multi mode optical fibers 11 were detected, to measure propagation loss in each of the optical fibers 11. The results are shown in Table 1 below. Note that in Table 1, the "Fiber Diameter" refers to the cladding diameter of the thinnest portion due to the tapering of each optical fiber. In addition, the "Tapering Rate" is defined as (cladding diameter which has been decreased by tapering)/(cladding diameter prior to tapering=125 μm). Generally, the ratio of core diameters with respect to cladding diameters of optical fibers is approximately 0.84. This ratio applies to each of the optical fibers in the evaluating systems. Therefore, the tapering rate represents the tapering rate of the core diameters.

TABLE 1

| Extension (mm) | Fiber Diameter (μm) | Tapering Rate (%) | Loss (%) |
|---|---|---|---|
| 0 | 125 | 0 | 0 |
| 1 | 110 | 12 | 1 |
| 3 | 100 | 20 | 2 |
| 6 | 80 | 36 | 2 |
| 9 | 50 | 40 | 3 |

As can be seen from the evaluation results of Table 1, when the tapering rate is 36%, the amount of loss is 2%. However, when the tapering rate increases above 36%, there is a possibility that the amount of loss will increase to 3%. Generally, 0.1 dB to 0.5 dB (2.3% to 10.9%) is the range of allowable amounts of loss for connectors that connect optical fibers. Therefore, it is desirable to suppress the amount of loss at the tapered portions to be 2% or less. Accordingly, it is preferable for the tapering rate of the light input portion of the light guide for endoscope of the present invention to be less than 36%. On the other hand, it is desired to increase the area illuminated by the illuminating light beam as much as possible at the light output portion. Therefore, the tapering rate of the light output portion is not limited to the aforementioned value, and may be set greater than 36%.

What is claimed is:

1. A light guide for endoscopes constituted by a plurality of multimode optical fibers, of which at least a portion is bundled, for propagating an illuminating light beam that enters from a first end facet thereof to a second end facet thereof, to emit the illuminating light beam onto a portion to be observed; the light guide comprising:
    a light input portion formed by the bundled plurality of multimode optical fibers; and
    a light output portion formed by the bundled plurality of multimode optical fibers;
    the light input portion and the light output portion being tapered to become narrower toward its respective end facet, while the number of multimode optical fibers at the light input portion and the light output portion are the same as that at other portions of the light guide; and
    the ends of each of the multimode optical fibers are also tapered at the light input portion and the light output portion.

2. A light guide for endoscopes as defined in claim 1, wherein:
    the tapering rate of the light input portion is less than 36%.

3. A light guide for endoscopes as defined in claim 2, further comprising:
    a concave transparent member, which is provided in close contact with the second end facet.

4. A light guide for endoscopes as defined in claim 3, further comprising:
    an imaging element provided at the second end facet, from which the illuminating light beam is output, for imaging the portion which is irradiated by the illuminating light beam.

5. A light guide for endoscopes as defined in claim 4, wherein:
    multimode optical fibers having outer diameters of 80 μm or less and greater than 60 μm including cladding portions, and core diameters within a range from 60 μm to 70 μm are employed as the multimode optical fibers.

6. A light guide for endoscopes as defined in claim 3, wherein:
    multimode optical fibers having outer diameters of 80 μm or less and greater than 60 μm including cladding portions, and core diameters within a range from 60 μm to 70 μm are employed as the multimode optical fibers.

7. A light guide for endoscopes as defined in claim 2, further comprising:
    an imaging element provided at the second end facet, from which the illuminating light beam is output, for imaging the portion which is irradiated by the illuminating light beam.

8. A light guide for endoscopes as defined in claim 7, wherein:
    multimode optical fibers having outer diameters of 80 μm or less and greater than 60 μm including cladding portions, and core diameters within a range from 60 μm to 70 μm are employed as the multimode optical fibers.

9. A light guide for endo scopes as defined in claim 2, wherein:
    multimode optical fibers having outer diameters of 80 μm or less and greater than 60 μm including cladding portions, and core diameters within a range from 60 μm to 70 μm are employed as the multimode optical fibers.

10. A light guide for endoscopes as defined in claim 1, further comprising:
    a concave transparent member, which is provided in close contact with the second end facet.

11. A light guide for endoscopes as defined in claim 10, further comprising:
    an imaging element provided at the second end facet, from which the illuminating light beam is output, for imaging the portion which is irradiated by the illuminating light beam.

12. A light guide for endo scopes as defined in claim 11, wherein:
    multimode optical fibers having outer diameters of 80 μm or less and greater than 60 μm including cladding portions, and core diameters within a range from 60 μm to 70 μm are employed as the multimode optical fibers.

13. A light guide for endo scopes as defined in claim 10, wherein:
    multimode optical fibers having outer diameters of 80 μm or less and greater than 60 μm including cladding portions, and core diameters within a range from 60 μm to 70 μm are employed as the multimode optical fibers.

14. A light guide for endoscopes as defined in claim 1, further comprising:

an imaging element provided at the second end facet, from which the illuminating light beam is output, for imaging the portion which is irradiated by the illuminating light beam.

15. A light guide for endo scopes as defined in claim 14, wherein:

multimode optical fibers having outer diameters of 80 μm or less and greater than 60 μm including cladding portions, and core diameters within a range from 60 μm to 70 μm are employed as the multimode optical fibers.

16. A light guide for endoscopes as defined in claim 1, wherein:

multimode optical fibers having outer diameters of 80 μm or less including cladding portions, and core diameters within a range from 60 μm to 70 μm are employed as the multimode optical fibers.

17. A light guide for endoscopes, as defined in claim 1, wherein the shapes of the facets of the multimode optical fibers at the light input portion and at the light output portion of both maximally densely filled structures.

\* \* \* \* \*